United States Patent [19]

Smith

[11] Patent Number: 5,315,110
[45] Date of Patent: May 24, 1994

[54] METAL CUP PRESSURE TRANSDUCER WITH A SUPPORT HAVING A PLURALITY OF THERMAL EXPANSION COEFFICIENTS

[75] Inventor: J. Douglas Smith, Houston, Tex.

[73] Assignee: ABB Vetco Gray Inc., Houston, Tex.

[21] Appl. No.: 85,068

[22] Filed: Jun. 29, 1993

[51] Int. Cl.$^5$ .............................................. H01J 5/16
[52] U.S. Cl. ............................ 250/227.27; 250/231.19; 356/358
[58] Field of Search ................... 250/227.27, 227.19, 250/227.29, 227.32, 231.19; 356/358, 356, 345, 445–448, 35.5; 73/705, 708, 715

[56] References Cited

U.S. PATENT DOCUMENTS

| | | |
|---|---|---|
| 4,682,500 | 7/1987 | Uda . |
| 4,859,844 | 8/1989 | Herman et al. . |
| 4,868,381 | 9/1989 | Davis . |
| 4,873,989 | 10/1989 | Einzig . |
| 4,897,542 | 1/1990 | Dakin et al. . |
| 4,904,863 | 2/1990 | McDearmon . |
| 4,944,187 | 7/1990 | Frick et al. . |
| 5,073,004 | 12/1991 | Clayton et al. . |
| 5,094,534 | 3/1992 | Cole et al. ................ 250/227.19 |
| 5,095,517 | 3/1992 | Monguzzi et al. . |
| 5,113,070 | 5/1992 | Smith . |
| 5,247,490 | 9/1993 | Goepel et al. ................ 356/358 |

Primary Examiner—David C. Nelms
Assistant Examiner—Que T. Le
Attorney, Agent, or Firm—James E. Bradley; Mark W. Handley

[57] ABSTRACT

An optical interferometer is provided for measuring downhole pressures by detecting a distance across a gap of an optical transmission pathway. The optical interferometer includes a pressure responsive member which, in response to downhole wellbore pressures, alters the distance between a light reflector and a lens. A partially reflective coating is deposited upon the pressure responsive member, which provides the light reflector, and the lens. The optical interferometer further includes a plurality of support members for the lens, with at least one of the plurality of support members having a different coefficient of thermal expansion from another support member so that when heated to downhole temperatures, thermal expansion of the support members will result in mutually offsetting displacements so that thermal expansion of the support members will not affect the gap over a range of downhole wellbore temperatures.

29 Claims, 3 Drawing Sheets

METAL CUP PRESSURE TRANSDUCER WITH A SUPPORT HAVING A PLURALITY OF THERMAL EXPANSION COEFFICIENTS

BACKGROUND OF THE INVENTION

1. Field of the Invention

This invention relates in general to instruments for detecting fluid pressures, and in particular to a Fabry-Perot optical interferometer which includes a metal cup pressure transducer for accurately monitoring downhole wellbore pressures over a range of operating temperatures.

2. Description of the Prior Art

Prior art pressure transducers have been proposed for monitoring downhole wellbore pressures in oil and gas wells. These pressures are monitored for determining downhole well conditions. By monitoring downhole wellbore pressures, conditions that are occurring within the wellbore and hydrocarbon bearing formations may be monitored so that production operations can be altered to maximize production of petroleum reservoirs.

Prior art electrically operated pressure transducers have been utilized. However, electrical and electronic pressure transducers present problems that arise when electrical signals are transmitted within wellbores. In general, there are many problems encountered in providing an insulated electrical conductor for transmitting electrical signals within wellbores. Electrical conductors are difficult to seal against exposure to wellbore fluids, which typically short electrical signals once they penetrate insulating materials around electrical conductors. Electrical conductors are also subject to corrosion and deterioration in harsh wellbore environments. Additionally, electrical transmissions are subject to electrical noises in some production operations.

Prior art optical interferometers have been proposed for measuring downhole wellbore pressures and temperatures. However, optical interferometers are typically very sensitive to temperature variations, and the downhole temperature of a specific position within a wellbore will change over time dependent upon different factors such as, for example, production rates, the types of fluids produced over the life of the well, and other downhole wellbore conditions. Additionally, it is difficult to determine what the precise downhole wellbore temperature will be at the position where an optical interferometer pressure transducer will be placed in the wellbore.

Prior art optical interferometer pressure transducers monitor pressures by passing an optical signal, or light, across a distance and measuring very small changes in that distance that occur in response to changes in pressure. Variations in temperatures in prior art optical interferometers can greatly affect and change the distance across which the light is passed for monitoring downhole wellbore pressures. Thus, prior art optical interferometers would be subject to erroneous readings due to changes in downhole wellbore temperatures.

Some prior art optical interferometer pressure transducers proposed for monitoring downhole wellbore pressures have utilized reference legs for comparing a measurement leg of an optical pathway to a reference leg, or reference optical pathway, which is disposed downhole within the wellbore with the measurement leg. However, inaccuracies arise due to differences between the measurement leg and a reference leg, and these differences are accurately compensated only at a specific downhole wellbore temperature.

Some prior art optical interferometer pressure transducers have attempted to utilize special materials to reduce the temperature coefficient of thermal expansion of pressure transducer members. However, since optical signals are used to measure a very small distance, very small variations in optical pathway distances can cause large errors in measured pressures, including those pressure transducers which utilize optical reference legs and those which utilize a Fabry-Perot type of measurement system.

SUMMARY OF THE INVENTION

It is one objective of the present invention to provide an optical interferometer for measuring downhole wellbore pressures by detecting a change in gap of an optical pathway, and which is not affected by exposure to different downhole temperatures within the wellbore.

It is another objective of the present invention to provide an instrument for detecting pressures within a wellbore by passing an optical signal between two reflective surfaces having a distance or gap therebetween which changes in proportion to the pressure being detected, and which is not affected by exposure to different downhole temperatures within the wellbore.

It is yet another objective of the present invention to provide a Fabry-Perot optical interferometer for detecting changes in wellbore pressures, and which will not be affected by changes in downhole wellbore temperatures.

The above objectives are achieved as is now described. An optical interferometer is provided for measuring downhole pressures by detecting a distance across a gap of an optical transmission pathway. The optical interferometer includes a pressure responsive member which, in response to downhole wellbore pressures, alters the distance between a reflector and a lens. The optical interferometer further includes a plurality of support members for the lens, with at least one of the plurality of support members having a different coefficient of thermal expansion from another support member so that when heated to downhole temperatures, thermal expansion of the support members will result in mutually offsetting displacements so that thermal expansion of the support members will not affect the gap over a range of downhole wellbore temperatures.

More particularly, the preferred embodiment of the present invention discloses a Fabry-Perot interferometer which includes a metal cup pressure transducer for downhole use within a wellbore. The metal cup pressure transducer includes at least one optical fiber which provides a wave guide for directing an optical signal from the surface of the wellbore and to an optical pathway extending between a lens and a reflective member. A pressure responsive member determines an optical transmission distance between the lens and the reflective member. The optical signal is passed between the lens and the reflective member, then returned uphole from the metal cup pressure transducer to optical processing equipment above the wellbore where the optical signal is processed to determine the transmission distance between the lens and reflective member. Pressure of production fluids within the wellbore may then be determined once the distance between the lens and the reflective surface is known.

The metal cup pressure transducer further includes a plurality of support members for supporting the lens and the reflective member within the metal cup pressure transducer. The support members are fabricated so that changes in downhole wellbore temperatures will not affect the distance between the lens and the reflective member during operations of the metal cup pressure transducer to monitor downhole wellbore pressures.

BRIEF DESCRIPTION OF THE DRAWING

The novel features believed characteristic of the invention are set forth in the appended claims. The invention itself however, as well as a preferred mode of use, and further objects and advantages thereof, will best be understood by reference to the following detailed description of an illustrative embodiment when read in conjunction with the accompanying drawings, wherein:

DETAILED DESCRIPTION OF THE INVENTION

Figure 1:
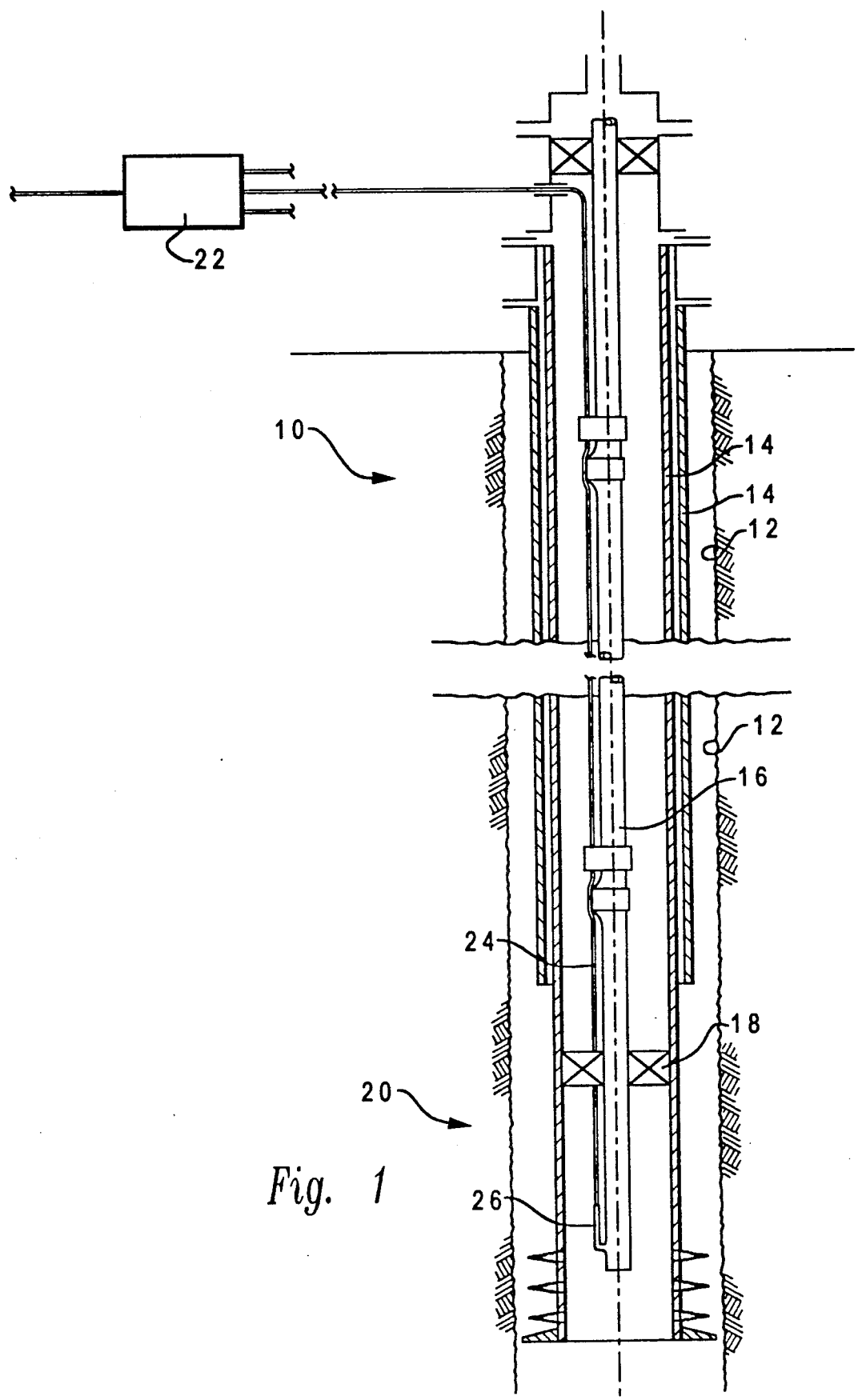
FIG. 1 is a longitudinal section view of a wellbore and schematically depicts the optical interferometer of the present invention.

Referring to FIG. 1, a longitudinal section view shows oil and gas well 10 having a wellbore 12 within which are two casing strings 14, production tubing 16, and production packer 18. Optical interferometer 20 of the preferred embodiment of the present invention is schematically depicted, with optical signal processor 22 shown above the surface of the wellbore, and fiber optic cable assembly 24 running within wellbore 12 to metal cup pressure transducer 26. Metal cup pressure transducer 26 is an instrument for use to optically measure the pressure of wellbore fluids, which are typically production fluids during production of oil and gas well 10.

Metal cup pressure transducer 26 is a Fabry-Perot interferometer which accepts an optical signal, light, and then modifies the optical signal to provide an output optical signal from which a wellbore pressure can be determined. There are numerous techniques for processing the output optical signal to determine the wellbore pressure, such as, for example, fringe counting. In the preferred embodiment of the present invention, a technique is used which determines a resonant frequency such as that shown in U.S. Pat. No. 4,859,844. Optical signal processor 22 is similar to the optical signal processor of U.S. Pat. No. 4,859,844, entitled "Comb Filter Pressure/Temperature Sensing System" issued on Aug. 22, 1989, invented by Herman et al, assigned to Hughes Aircraft Company, and which is hereby incorporated by reference as if fully set forth herein.

Figure 2:
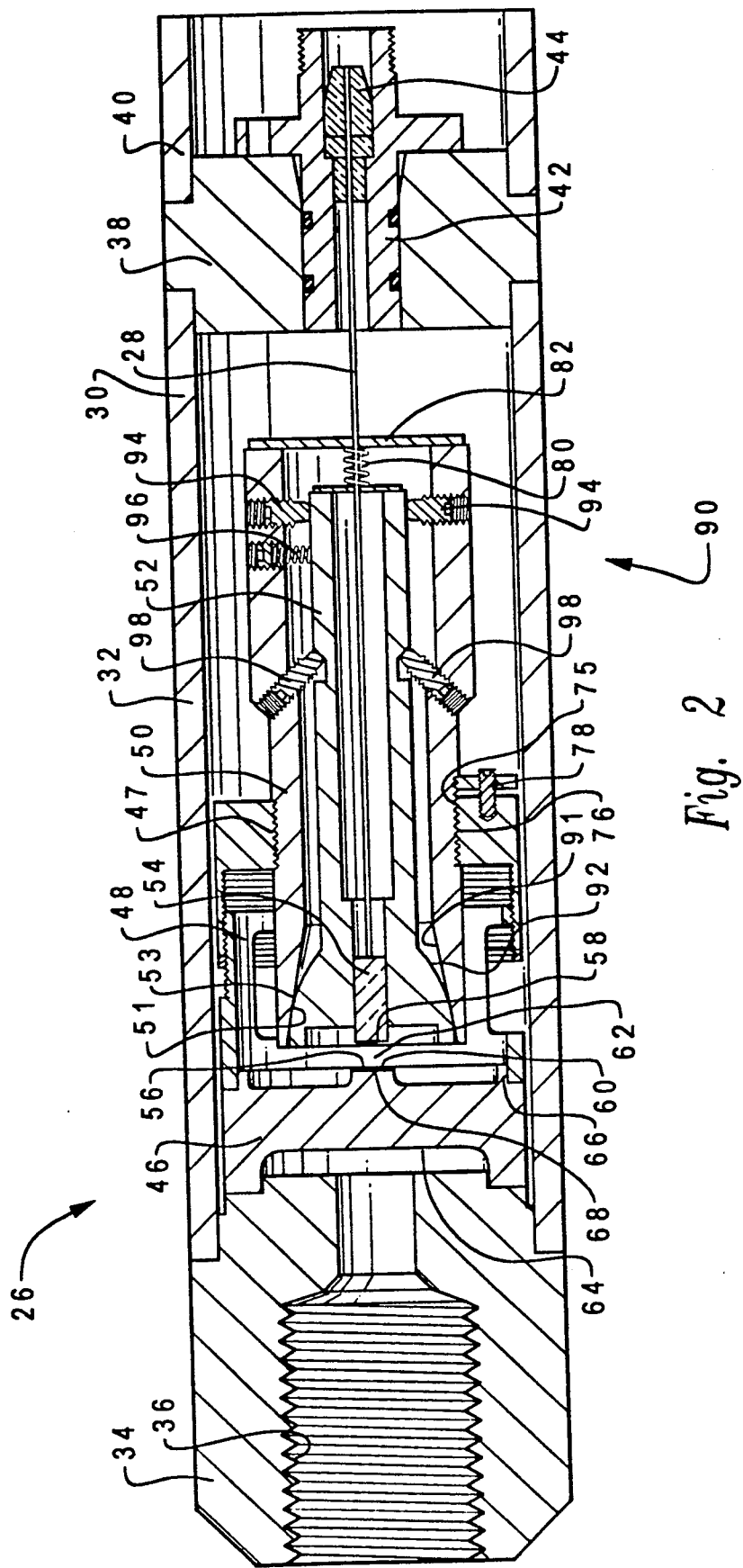
FIG. 2 is longitudinal section view of the metal cup pressure transducer of the present invention.

Referring now to FIG. 2, a longitudinal section view depicts metal cup pressure transducer 26 of the preferred embodiment of the present invention, which is a Fabry-Perot optical pressure transducer. Optical fiber 28 provides an optical waveguide, or an optical pathway, for receiving an optical signal from, and transmitting an optical signal to fiber optic cable assembly 24 (shown in FIG. 1), and extends within metal cup pressure transducer 26. Metal cup pressure transducer 26 includes outer housing 30, having sleeve 32 and pressure head 34 which, in the preferred embodiment of the present invention, is electron beam welded to sleeve 32. An interior end of pressure head 34 includes threads 36 to which a male coned and threaded pressure fitting, such as, for example, high pressure type F-C fitting available from Autoclave Engineering, Inc. of Erie, Pa. A coned and threaded pressure fitting may be connected for passing fluids into metal cup pressure transducer 26 for detecting the pressure of such fluids. In the preferred embodiment of the present invention, metal cup pressure transducer 26 is utilized to measure the downhole pressure of production fluids within wellbore 12. Downhole pressures within wellbore 12 may then be used for detecting production problems within wellbore 12, and for monitoring production parameters of the formation from which the production fluids flow.

Still referring to FIG. 2, housing 30 further includes bulkhead 38 which is electron beam welded to sleeve 32 and skirt 40. Connector 42 extends within a central bore of bulkhead 38 with a pair of O-rings sealing therebetween. Ceramic connector 44 is a ceramic ferrile which secures optical fiber 28 within connector 42. Fiber optic cable assembly 24 (shown in FIG. 1) fastens to connector 42 for optically coupling optical fiber 28 to optical signal processor 22 (shown in FIG. 1). Diaphragm 46, which is a metal cup in the preferred embodiment of the present invention, is secured within housing 30 by electron beam welding to pressure head 34. Diaphragm 46 provides a pressure responsive member.

Support means 47 includes support head 48, swivel support 50, and swivel member 52, which extend longitudinally within housing 30. Support head 48 is press fit onto diaphragm 46, swivel support 50 threadingly secures within support head 48, and swivel member 52 is secured within swivel support 50 by lock screws as discussed below.

Optical fiber 28 extends within swivel member 52, and has an end face connected to GRIN lens 54. Optical fiber 28, although shown as taught in FIG. 2, is actually slack when metal cup pressure transducer 26 is fully assembled. In fact, an excess portion of optical fiber 28 may be coiled between swivel support 50 and bulkhead 38 within housing 30.

GRIN lens 54 is a commercially available lens which provides a lens means for passing a portion of an optical signal passed downhole through optical fiber 28 to GRIN lens 54, and for reflecting a portion of the optical signal back uphole through optical fiber 28. The reflective index of GRIN lens 54 varies in a radial direction across GRIN lens 54 so that light passing through GRIN lens 54 will be focused toward reflective surface 56. The radially outer portions of GRIN lens 54 have a higher reflective index than the radially inner portions of GRIN lens 54. In the preferred embodiment, GRIN lens 54 is formed from silicon dioxide ($SiO_2$).

In the preferred embodiment of the present invention, a light reflector is provided by reflective surface 56, which is formed on diaphragm 46 by grinding and polishing the central end portion of metal cup diaphragm 46. Reflective surface 56 provides a reflective member which is formed integrally with metal cup diaphragm 46. An optical signal passes through optical fiber 28 and GRIN lens 54 to reflective surface 56, which reflects the optical signal back through GRIN lens 54 and to optical fiber 28.

In the preferred embodiment of the present invention, multi-layer coating 58 is applied to GRIN lens 54 by vapor deposition. Additionally, multi-layer coating 60 is applied to reflective surface 56. Multi-layer coatings 58 and 60 are reflective coatings which are applied for determining a reflectivity for GRIN lens 54 and reflective surface 56 to control the finesse of metal cup pressure transducer 26. Finesse is a measure of the quality of the optical signal which returns from metal cup pressure transducer 26 to uphole optical signal processor 22 (shown in FIG. 1). Multi-layer coating 58 is added to the surface of GRIN lens 54 to increase the reflectivity for GRIN lens 54. In the preferred embodiment of the present invention, both GRIN lens 54 and reflective surface 56 have a reflectivity of 40 percent.

Still referring to FIG. 2, gap 62 extends between the face of GRIN lens 54 and the face of reflective surface 56. Gap 62 provides an optical pathway through which an optical signal is transmitted over an optical transmission distance. The optical transmission pathway through gap 62 changes in optical transmission distance in response to the level of pressure being measured.

In the preferred embodiment of the present invention, diaphragm 46 is a metal cup which provides a pressure responsive member. Diaphragm 46 has a diameter-to-thickness ratio of approximately 3.75 to 1 in the preferred embodiment of the present invention, and 12,000 pounds per square inch of pressure acting across diaphragm 46 results in 35 microns of displacement. Diaphragm 46 includes wetted surface 64 which, in the preferred embodiment of the present invention, is exposed to wellbore fluids for which metal cup pressure transducer is utilized for monitoring the pressure thereof. Diaphragm 46 further includes annular protrusion 66 and tip 68. Tip 68 is the central portion of diaphragm 46 which is ground and then coated with multi-layer reflective coating 60 to provide reflective surface 56. Although in the preferred embodiment of the present invention, reflective surface 56 is made integrally with diaphragm 46, in other embodiments of the present invention, reflective surface 56 may be provided by a reflective member which is not made integrally with diaphragm 46.

Annular protrusion 66 and tip 68 have end faces which extend from diaphragm 46 into a singular plane which is perpendicular to a longitudinal axis of housing 30. The end faces of annular protrusion 66 and tip 68 extend in the same singular plane so that reflective surface 56 will extend the same distance from diaphragm 46 along a longitudinal axis direction as annular protrusion 66 extends to mate with support head 48. This configuration is utilized to prevent thermal expansion of diaphragm 46 from changing the distance across gap 62.

Figure 3:
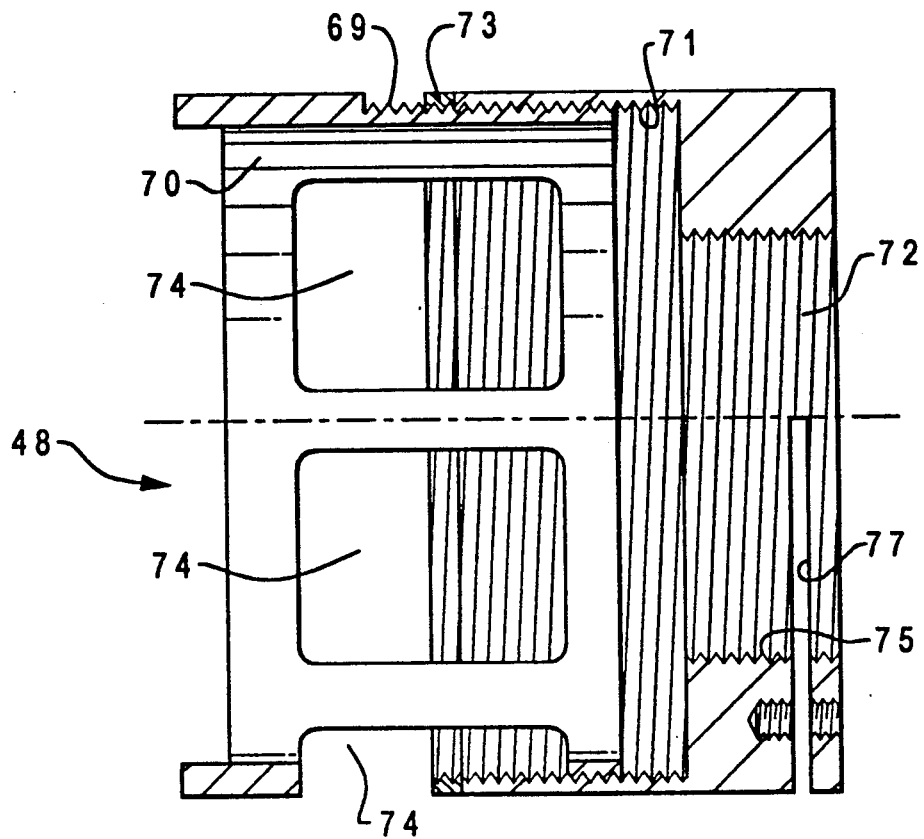
FIG. 3 is a longitudinal section view depicting a support member of the present invention.

Referring to FIG. 3, support head 48 includes a first half 70 and a second half 72. Threads 69 of first half 70 engage threads 71 of second half 72 to threadingly secure first half 70 to second half 72 and allow adjustment of the length of support head 48. Lock nut 73 is utilized to lock first half 70 with respect to second half 72 once a length for support head 48 has been adjusted by rotating first half 70 with respect to second half 72. First half 70 is formed from a material which has a different coefficient of thermal expansion from the material from which second half 72 is formed. Further a plurality of windows 74 are cut through the cylindrical wall of first half 70 of support head 48 to allow for visual inspection to initially align GRIN lens 54 with reflective surface 56.

Support head 48 also includes internal threads 75 for mating with external threads 76 of swivel support 50 (shown in FIG. 2). In the preferred embodiment of the present invention, threads 69 and 71 have 42 threads per inch and threads 75 and 76 have 40 threads per inch. The difference in the number of threads per inch allows for variable adjustment between the two sets of threads as the metal cup pressure transducer is calibrated. Slot 77 passes transversely through an end portion of second half 72 and threads 75. Still referring to FIG. 3, it should be noted that different materials may be selected, and that different longitudinal lengths for first half 70 and second half 72 can be selected to provide an overall composite, or gross coefficient of thermal expansion for support head 48.

Referring to FIGS. 2 and 3, the gross coefficient of thermal expansion for support head 48 may be selectively adjusted by changing the longitudinal lengths of first half 70 and second half 72, and changing the materials from which they are made, to match the coefficient of thermal expansion for the combination of swivel support 50, swivel member 52 and GRIN lens 54 so that the distance across gap 62 will not change when metal cup pressure transducer is exposed to a range of different wellbore temperatures. Different gross coefficients of thermal expansions are required since the presence of longitudinally extending gap 62 requires equal longitudinal thermal displacements in opposite longitudinal directions by two different sets of support members which do not have equal lengths in the longitudinal directions.

Referring to FIG. 2, swivel support 50 extends within support head 48 and is threadedly connected to support head 48 by threads 75 and 76. Support head 48 includes support head lock screw 78 for locking internal threads 75 within support head 48 onto external threads 76 on swivel support 50 to lock the threaded connection and retain swivel support 50 in place within support head 48. Slot 77 (shown in FIG. 3) passes transversely into second half 72 (shown in FIG. 3) to provide mechanical advantage for lock screw 78 in squeezing threads 75 onto threads 76. Swivel support 50 is selectively adjustable by rotating within support head 48 at threads 75 and 76 to adjust the distance across gap 62, and thus select an initial optical transmission distance of the optical pathway through gap 62. Tension spring 80 extends from cross member 82 of swivel support 50 for pulling swivel member 52 longitudinally into swivel support 50.

Figure 4:
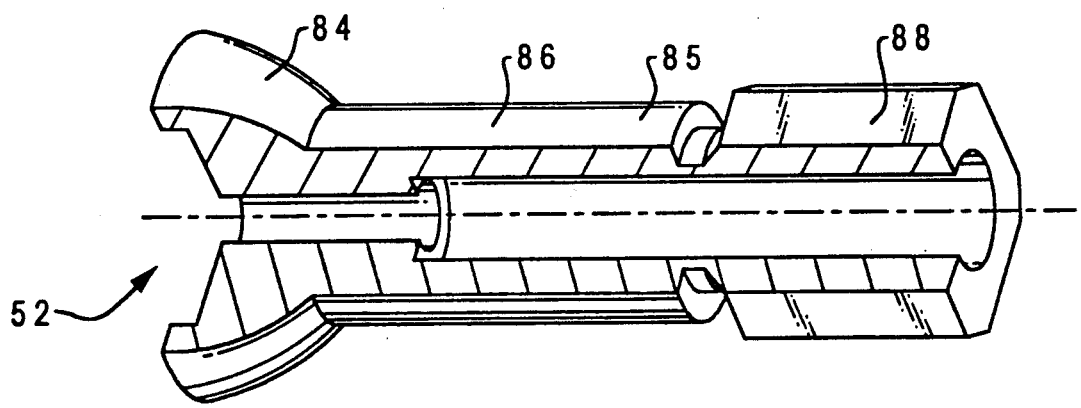
FIG. 4 is a one-quarter longitudinally sectioned perspective view depicting the swivel member of the present invention.

Referring to FIG. 4, swivel member 52 is provided by an elongated member having spherically radiused head 84 and shank 85, which includes cylindrical central section 86, and rectangular end section 88, which all share a central longitudinal axis. Swivel member 52 includes rectangular section 88 to provide mutually perpendicular surfaces for an adjustment means, which is discussed below, to press against in aligning GRIN lens 54 with reflective surface 56. Referring again to FIG. 2, since metal cup pressure transducer is a Fabry-Perot optical pressure transducer, the end face of GRIN lens 54 should be kept parallel to reflective surface 56 to insure proper reflection of the optical signal from surface 56 and transmission of the optical signal across gap 62 therebetween, and to insure that the optical signal returning from metal cup pressure transducer 26 to optical sensor processor 22 (shown in FIG. 1) will be suitable for processing to determine the downhole pressure within wellbore 12.

The axis of swivel member 52 is substantially coaxial with the axis of outer housing 30, but it can be angled slightly relative to the housing 30 axis by adjustment means 90 controlling engagement between internal surface 91 of swivel support 50 and external surface 92 of swivel member 52. Adjustment means 90 includes swivel adjustment screws 94, compression springs 96, and axial lock screws 98. Adjustment means 90 is provided for pivoting swivel member 52 within swivel support 50 to align the end face of GRIN lens 54 with reflective surface 56 so that the end face of GRIN lens 54 is parallel to reflective surface 56.

There are four radially extending swivel adjustment screws 94, positioned circumferentially around the rectangular end section 88 of swivel member 52, spaced 90° degrees apart. Additionally, two compression springs 96 are provided at a 90° degree spacing between the two. Compression springs 96 are provided to push against rectangular end section 88 (shown in FIG. 4) of swivel member 52 to urge swivel member 52 to move when swivel adjustment screws 94 are rotated to urge swivel member 52 to swivel for adjusting the end face of GRIN lens 54 into parallel alignment with reflective surface 56. Two axial lock screws 98 are provided at 180° degrees spacings from each other to press against a bevelled surface between cylindrical central section 86 and rectangular end section 88 (shown in FIG. 4) of swivel 52 for locking swivel member 52 against moving axially within swivel support 50 once proper adjustments have been made with swivel adjustment screws 94.

In the preferred embodiment of the present invention, metal cup diaphragm 46 is formed from a nickel alloy material, available from Inco Alloy International, and specified as NI-SPAN-C alloy 902. This material was chosen to form diaphragm 46 from its mechanical characteristics which provide for low hysteris. Swivel support 50 and swivel member 52 are formed from Kovar, which is a material having mechanical properties to provide a low coefficient of thermal expansion. Pressure head 34 and bulk head 38 are formed from 316 stainless steel. Sleeve 32 and skirt 40 are formed from 17-4 P.H. stainless steel. Reflective multi-layer coatings 58 and 60 are provided by vapor depositing multiple layers of magnesium oxide and silicon oxide to select the reflectivity for both the end face of GRIN lens 54 and reflective surface 56.

Referring to FIG. 3, support head 48 includes first half 70, which is formed of stainless steel, and second half 72, which is formed from Kovar, which are threadingly coupled and locked into a relative position by lock nut 73. Support head 48 is formed to have a selected gross coefficient of thermal expansion to insure that when transducer 26 is exposed to varying wellbore temperatures, gap 62 will not be changed since the thermal displacement of support head 48 will be equivalent to the combined thermal displacement of swivel support 50, swivel member 52, and GRIN lens 54 to maintain the end face of GRIN lens 54 the same distance from reflective surface 56.

In other embodiments of the present invention, first half 70 and second half 72 may be formed from other materials to provide a selectable gross coefficient of thermal expansion for support head 78 to thermally expand and offset the overall combined thermal expansion of swivel support 50, swivel member 52, and GRIN lens 54. For example, steel can be used for a material having a middle range for a coefficient of thermal expansion, Invar and Kovar can be used for materials having low range coefficients of thermal expansion, and aluminum can be used for a material having a high range coefficient of thermal expansion. A middle to low range gross coefficient of thermal expansion for support head 48 can be provided by forming first half 70 from Invar, and forming second half 72 from steel. To provide support head 48 with a gross coefficient of thermal expansion which is between the middle to the high end of the range for coefficients of thermal expansion, first half 70 could be made of aluminum and second half 72 could be made from steel. For a low range coefficient of thermal expansion, Kovar could be substituted for Invar, aluminum, or steel. Additionally, different longitudinal lengths may be chosen for first half 70 and second half 72 so that they provide different proportions of overall length for support head 48.

Thus, by choosing different materials and different longitudinal length proportions for halves 70 and 72, the gross, or composite, coefficient thermal expansion for support head 48 may be tuned, or selectably adjusted, so that for different temperature ranges and different lengths of materials from which swivel support 50, swivel member 52 and GRIN lens 54 are made, downhole temperature variations will not affect the length of the optical transmission pathway across gap 62. It should also be noted that, in other embodiments of the present invention, support head 48 may be formed from a singular member, from two members such as first half 70 and second half 72, or from more than two members.

By proper selection of the materials and lengths of the component members for support head 48, swivel support 50, and swivel member 52, to provide different gross coefficients of thermal expansion for these members, thermal displacements by each of these members are combined to offset any displacement which the other members undergo due to exposure to temperatures to which metal cup pressure transducer 26 is exposed. In effect, support head 48 is a first cylinder within which swivel support 50 is nested, and swivel support 50 is a second cylinder within which swivel member 52, a third cylinder, is nested. This nested cylinder arrangement allows for cascading the coefficients of thermal expansions for these different members so that they combine to cancel out any thermal displacement between them to prevent variations in temperatures from changing gap 62, which, referring back to FIG. 2, is between the end face of GRIN lens 54 and reflective surface 56.

Still referring to FIG. 2, metal cup pressure transducer 26 is calibrated prior to use within a wellbore. Gap 62 is first set at an initial distance by rotating swivel support 50 within support head 48. Additionally, alignment of swivel member 52 within swivel support 50 is initially set.

The metal cup pressure transducer 26 is then operated at room temperatures and gap 62 adjusted by rotating swivel support 50 within support head 48, and swivel member 52 within swivel support 50, to optimize the output signal from metal cup pressure transducer 26. Swivel adjustment screws 94 are used to adjust the alignment of swivel member 52 within swivel support 50. Axial lock screws 98 can be used to lock swivel member 52 within swivel support 50 once GRIN lens 54 is aligned with reflective surface 56.

After setting at room temperatures, metal cup pressure transducer 26 is placed within a calibration oven and heated to a downhole wellbore temperature, such as, for example, 300° degrees Fahrenheit. A shift in the output signal that results from exposure to the downhole wellbore temperature is compensated for by adjusting support head 48 to thermally expand to offset thermal expansion by swivel support 50, swivel member 52, and GRIN lens 54.

Referring to FIGS. 2 and 3, support head 48 is adjusted, or tuned, to have a different overall displacement due to thermal expansion by rotating first half 70 within second half 72. Additionally, swivel support 50 can be rotated within support head 48. Since threads 69 and 71 have 42 threads per inch, and threads 75 and 76 have 40 threads per inch, one rotation with threads 69 and 71 will be different than one rotation with threads 75 and 76 to allow for a difference in adjustment. Once proper adjustments have been made, lock nut 73 may be tightened to hold support head 48 in adjustment, and support head lock screw 78 may be tightened to close slot 77 and prevent swivel support 50 from rotating within support head 48.

Operation of optical interferometer 20 is now described. Referring to FIG. 1, metal cup pressure transducer 26 is lowered within wellbore 12 secured to production tubing 16, with fiber optic cable assembly 24 connecting metal cup pressure transducer 26 to optical signal processor 22, which is located at the ground surface above well 10. Optical interferometer 20 is utilized for measuring downhole wellbore pressures to monitor the pressure of production fluids produced from a hydrocarbon bearing formation through which the lower end of wellbore 12 passes. A broad frequency band optical signal is sent from optical signal processor 22, and down fiber optic cable assembly 24 to metal cup pressure transducer 26. The pressure within wellbore 12 acts upon metal cup pressure transducer 26, which alters the optical signal sent from optical signal processor 22 to provide an optical signal from which the pressure within wellbore 12 can be determined. Then, the altered optical signal is sent uphole to optical signal processor 22. Optical signal processor 22 processes the altered optical signal and generates an output signal which indicates the downhole pressure of production fluids within wellbore 12.

Referring now to FIG. 2, the operational details of metal cup pressure transducer 26 are discussed. Wellbore fluid pressing against wetted surface 64 of diaphragm 46 urges metal cup diaphragm 46 to expand in a longitudinal direction of metal cup pressure transducer 26 so that reflective surface 56 is moved towards the end face of GRIN lens 54, shortening gap 62. An optical signal is transmitted downhole, and through optical fiber 28 to GRIN lens 54. Multi-layer coating 58 on GRIN lens 54 reflects a first portion of the optical signal back into GRIN LENS 54. A second portion of the optical signal is transmitted through GRIN lens 54, passed through gap 62 and to reflective surface 56. Reflective surface 56 then reflects the second portion of the optical signal back through gap 62 and to GRIN lens 54. The second portion of the optical signal constructively and destructively interferes with the first portion of the reflected optical signal. The resulting multi-frequency beam interference signal then passes through GRIN lens 54, back to optical fiber 28, and back uphole to optical signal processor 22 (shown in FIG. 1).

It should be noted that a portion of the optical signal transmitted downhole will actually reflect multiple times between the end face of GRIN lens 54 and reflective surface 56, although the above discussion discusses a second portion of the optical signal from the surface in simplified form by describing a second portion of the optical signal which passes from GRIN lens 54, to reflective surface 56, back to GRIN lens 54, and through optical fiber 28. Since metal cup pressure transducer 26 is a Fabry-Perot interferometer, a multi-frequency beam interference optical signal is passed uphole.

The resulting interference pattern from the first and second portions of the optical signal is transmitted uphole to optical signal processor 22 to determine the optical transmission distance across gap 62. In the preferred embodiment of the present invention, the resulting interference optical signal is analyzed to determine the frequency of most strongly constructively reinforced portion of the multi-frequency beam interference signal from the metal cup pressure transducer 26, which indicates the distance across gap 62. Since the distance across gap 62 is determined by the pressure with which production fluids press against wetted surface 64 of diaphragm 46, the pressure of the production fluids may be determined by measuring the distance across gap 62. As the pressure with which production fluids press against wetted surface 64 increases, gap 62 between GRIN lens 54 and reflective surface 56 decreases. As gap 62 changes, the wavelength and corresponding frequency of the most strongly reinforced portion of the multi-frequency beam interference signal changes. In addition to determining the wavelengths of the most strongly constructively reinforced portion of the optical signal, changes in gap 62 also change the timing of wavelength phase between the first and second portions of the optical signal for particular wavelengths.

The metal cup pressure transducer of the preferred embodiment of the present invention offers several advantages over prior art of pressure transducers. First, since an optical signal is used rather an electrical signal, problems with transmitting electrical signals within a wellbore are not incurred. Unlike an electrical conductor, an optical fiber passes an optical signal, which is light, and can still transmit an optical signal if it is exposed to moisture. The optical fiber should lose only its ability to pass an optical signal if it is broken.

The present invention provides an optical pressure transducer with improved reliability over the reliability of prior art electronic pressure transducers. Optical components are less susceptible to temperature variations, such as, for example, prior art electrically operated strain gauges. Discreet optical components are used, such as the GRIN lens which is made out of silicon dioxide which are more tolerant to high temperature applications than prior art electrically operated components, which typically require temperature compensating components in addition to temperature sensitive measurement components.

Additionally, since the net combined displacement of support members due to thermal expansion is prevented, the optical transmission distance across an optical transmission pathway gap remains the same over a wider range of temperature variations for a constant pressure. Thus the metal cup pressure transducer of the present invention will more accurately perform over a wider range of temperatures such as occur over the productive life of an oil and gas well at a selected depth through which production fluids pass.

Further, the metal cup pressure transducer of the present invention provides a plurality of support members which may be utilized for adjusting an optical transmission distance across an optical pathway, or gap, and for aligning a GRIN lens and reflective surface to be parallel for passing an optical signal therebetween.

This plurality of support members is selected to have offsetting coefficients of thermal expansion so that the net, combined, thermal displacement in the direction of the optical transmission pathway is substantially zero.

Although the invention has been described with reference to a specific embodiment, this description is not meant to be construed in a limiting sense. Various modifications of the disclosed embodiment as well as alternative embodiments of the invention will become apparent to persons skilled in the art upon reference to the description of the invention. It is therefore contemplated that the appended claims will cover any such modifications or embodiments that fall within the true scope of the invention.

What is claimed is:

1. An optical interferometer for use in a wellbore to measure a wellbore pressure by passing an optical signal through an optical pathway, and detecting a change in a distance across the optical pathway, the optical interferometer comprising:
    a housing for lowering within the wellbore to a downhole wellbore depth;
    at least one optical fiber for providing a waveguide to direct the optical signal within the housing and to the optical transmission pathway;
    a lens means secured within the housing for receiving the optical signal from the at least one optical fiber, directing at least a portion of the optical signal through the optical pathway, and further for passing the portion back into the at least one optical fiber;
    a light reflector secured within the housing spaced opposite of the lens means by a gap, which defines at least a portion of the optical pathway;
    the lens means and the light reflector secured within the housing for directing the portion of the optical signal from the lens means, through the gap, to the light reflector, back through the gap, and to the lens means for passing into the at least one optical fiber;
    a pressure responsive means secured within the housing for urging the light reflector to move with respect to the lens means to change the gap in response to changes in the wellbore pressure for providing the change in the distance across the optical pathway; and
    a support means for securing the lens means and pressure responsive means within the housing, the support means having a plurality of coefficients of thermal expansion for providing a plurality of mutually offsetting displacements in response to a temperature change, wherein the mutually offsetting displacements prevent the temperature change from changing the distance across the gap.

2. The optical interferometer of claim 1, wherein the pressure responsive means is a diaphragm and wherein the light reflector is formed from a surface of the diaphragm.

3. The optical interferometer of claim 2, wherein the light reflector comprises:
    a coating applied to the surface of the diaphragm to determine a reflectivity for the surface.

4. The optical interferometer of claim 1, wherein the lens means comprises:
    a lens member; and
    a partially reflective coating applied to an end of the lens member to determine a reflectivity for the lens means.

5. The optical interferometer of claim 4, wherein the lens member is a GRIN lens.

6. The optical interferometer of claim 1, wherein the lens means is a GRIN lens.

7. The instrument of claim 1, wherein a multi-layer coating is vapor deposited onto the lens means and the light reflector for determining a quality of output optical signal from the optical inferometer.

8. The optical interferometer of claim 1, wherein the support means further comprises:
    a swivel means for selectably aligning an end face of the lens means to be parallel with a reflective surface of the light reflector.

9. The optical interferometer of claim 1, wherein the support means further comprises:
    a support head for selectably tuning the support means to have a composite coefficient of thermal expansion which prevents the temperature change from changing the distance across the gap.

10. The optical interferometer of claim 1, wherein the support means comprises:
    the housing having a longitudinal axis, a first end and a second end;
    the pressure responsive means being mounted to the first end, with the light reflector located on the longitudinal axis;
    a swivel support means mounted coaxially in the housing, and having an internal swivel surface;
    a swivel member having an axis and being mounted in the swivel supported by the swivel member having an external swivel surface that engages the internal swivel surface to allow angular adjustment of the swivel member axis relative to the longitudinal axis of the housing, the lens means being mounted in the swivel member, with the fiber extending from the second end of the housing to the swivel member;
    the swivel member having a shank extending from the external swivel surface toward the second end of the housing, the shank being located in the swivel support and spaced therefrom by an annular clearance; and
    a plurality of screws extending laterally from the swivel support through the annular clearance into engagement with the shank to support the swivel member at a selected angular position relative to the longitudinal axis of the housing.

11. The optical interferometer of claim 10, wherein the swivel member further comprises:
    a spherically radiused head within which the lens means is secured, the spherically radiused head providing the external swivel surface for engaging with the external swivel surface of the swivel support; and
    the shank included a rectangular section for providing mutually perpendicular surfaces for at least a portion of the plurality of screws to support for urging the swivel member into the selected angular position.

12. The optical interferometer of claim 10, wherein the support means further comprises:
    a support head coaxially secured within the housing to the pressure responsive member;
    a swivel support coaxially secured within the support head, and within which the swivel member is secured; and
    a means for adjusting the alignment of the swivel support within the support head along a longitudinal axis of the housing for initially setting the optical transmission distance at a predetermined gap.

13. The optical interferometer of claim 12, wherein the support head comprises:
a first half and a second half which have different coefficients of thermal expansion, and which are longitudinally adjustable relative to each other for tuning the support head to have a combined coefficient of thermal expansion for mutually offsetting a combined thermal displacement by the swivel support, the swivel member, and the lens means to prevent the temperature change from changing the optical transmission distance.

14. An instrument for use in a wellbore to measure a wellbore pressure by receiving an input optical signal, and transmitting an output optical signal which varies in response to changes in the wellbore pressure, the instrument comprising:
a outer housing having a longitudinal axis, a first end and a second end;
a swivel support means mounted coaxially within the outer housing, and having an internal swivel surface;
a swivel member having an axis and being mounted in the swivel support supported by the swivel member having an external swivel surface that engages the internal swivel surface to allow angular adjustment of the swivel member axis relative to the longitudinal axis of the housing;
the swivel member having a shank extending from the external swivel surface toward the second end of the outer housing, the shank being located in the swivel support and spaced therefrom by an annular clearance;
a plurality of adjustment members extending laterally from the swivel support, through the annular clearance, and into engagement with the shank to support the swivel member at a selected angular position relative to the longitudinal axis of the housing;
at least one optical fiber extending through the first end of the outer housing and into the swivel member to provide at least one waveguide for directing the input optical signal into the outer housing, and passing the output signal from the outer housing;
a lens means mounted within the swivel member for receiving the input optical signal from the at least one optical fiber, passing at least a portion of the input optical signal to an optical pathway, and passing at least a portion of the output optical signal to the at least one optical fiber;
a light reflector disposed within the outer housing and aligned with the lens means for receiving the portion of the input optical signal from the lens means, and directing the portion of the input optical signal back towards the lens means;
a pressure responsive means mounted in the second end of the outer housing for at least in part determining an optical transmission distance between the lens means and the light reflector in response to the wellbore pressure; and
the swivel support means having a plurality of coefficients of thermal expansion for providing a plurality of mutually offsetting displacements in response to a temperature change, wherein the mutually offsetting displacements prevent the support means from changing the optical transmission distance in response to the temperature change.

15. The instrument of claim 14, wherein the plurality of adjustment members include a plurality of screws which are rotated within the support means to urge the swivel member into the selected angular position relative to the longitudinal axis of the housing for aligning the lens means with the light reflector.

16. The instrument of claim 14, wherein the swivel member further comprises:
a spherically radiused head for providing the external swivel surface, and within which the lens means is secured; and
the shank having a rectangular section for providing mutually perpendicular surfaces for engaging at least a portion of the plurality of adjustment members.

17. The instrument of claim 14, wherein the light reflector is formed from the pressure responsive member.

18. The instrument of claim 17, wherein the light reflector comprises:
a coating applied to the surface of the pressure responsive member to determine an index of refraction for the surface.

19. The instrument of claim 14, wherein the lens means comprises:
a lens member; and
a partially reflective coating applied to an end of the lens member to determine an index of refraction for the lens means.

20. The instrument of claim 14, wherein the lens means reflects a reflected portion of the input optical signal back into the at least one optical fiber, and the reflected portion provides a portion of the output optical signal.

21. The instrument of claim 14, wherein the swivel support means includes:
a support head coaxially secured within the outer housing to the pressure responsive member;
a swivel support coaxially secured within the support head, and within which the swivel member is secured; and
a means for adjusting the alignment of the swivel support within the support head along a longitudinal axis of the outer housing for initially setting the optical transmission distance at a predetermined gap.

22. The instrument of claim 16, wherein the support head comprises:
a first half and a second half which have different coefficients of thermal expansion, and which are longitudinally adjustable relative to each other for tuning a combined coefficient of thermal expansion for the support head to mutually offset a thermal displacement by a combination of the swivel support, the swivel member, and the lens means to prevent the temperature change from changing the optical transmission distance.

23. A method for use in a wellbore to determine a wellbore pressure by passing an optical signal through an optical transmission pathway, and detecting a change in a distance across the optical transmission pathway, the method comprising the steps of:
securing a pressure responsive member and a support means together within a housing, the support means having a support head, a swivel support, and a swivel member which have mutually offsetting coefficients of thermal expansion to prevent a temperature change from changing the distance across the optical transmission pathway, and the pressure responsive member secured within the housing for moving in response to a change in the wellbore pressure;

securing a lens means and a light reflector within the housing and separated by a gap which defines at least part of the distance across the optical transmission pathway, one of the lens means and the light reflector secured to the support means, and the other of the lens means and the light reflector connected to the pressure responsive member for the pressure responsive member to urge a change in the gap in response to a change in the wellbore pressure;

positioning a fiber optic cable adjacent to the lens means for passing the optical signal to the lens means, and for receiving at least a part of the optical signal from the lens means;

adjusting the support means to select an initial distance across the gap, and to align the lens means with the light reflector for passing a portion of the optical signal therebetween;

securing the housing to a fiber optic cable assembly and a downhole well tool;

lowering the downhole well tool and housing within the wellbore to a downhole wellbore depth; and passing the optical signal through the optical fiber and to the lens means, which passes at least a portion of the optical signal across the gap to the light reflector, which then reflects the portion of the optical signal back to the lens means for transmission through the lens means and into the optical fiber for passing through the optical fiber.

24. The method of claim 23, wherein the step of adjusting the support means to select an initial distance across the gap comprises the steps of:

rotating the swivel support within the support head to engage a screw thread on the swivel support within a screw thread within the support head and move the lens means linearly with respect to the light reflector; and locking the swivel support into position with a lock screw after an initial distance across the gap has been selected.

25. The method of claim 23, wherein the step of adjusting the support means to align the lens means with the light reflector for passing the portion of the optical signal therebetween comprises the steps of:

rotating a plurality of adjustment screws to pivot the swivel member within the swivel support about a longitudinal axis of the housing to move the lens means into alignment with the light reflector; and locking the swivel member into position with at least one axial lock screw once the lens means is moved into alignment with the light reflector for passing the portion of the optical signal therebetween.

26. The method of claim 23, wherein the support head is tuned to have mutually offsetting coefficients of thermal expansion for preventing the temperature change from changing the distance across the gap, and the method of tuning the support head comprises the steps of:

providing the support head with a first and second members having different coefficients of thermal expansion, and which are connected by a plurality of mating screw threads;

rotating the first member with respect to the second member to select the proportion of which each of the first and second members make up a total length of the support head; and locking the first member with respect to the second member to prevent relative rotation therebetween and to lock a gross coefficient of thermal expansion into the support head.

27. The method of claim 23, further comprising the step of:

coating a surface of the pressure responsive member to determine a reflectivity for the end surface and to provide the light reflector.

28. The method of claim 23, further comprising the step of:

applying a partially reflective coating to the lens means to determine a reflectivity for the lens means.

29. The method of claim 23 further comprising the step of:

vapor depositing multiple layers of a partially reflective coating onto the lens means and the light reflector to determine a reflectivity for each to control the quality of the optical signal passed from the lens means and into the at least one optical fiber.

* * * * *